United States Patent
Lim et al.

(10) Patent No.: US 9,737,236 B2
(45) Date of Patent: Aug. 22, 2017

(54) GAS CONCENTRATION APPARATUS HAVING CARBON FOAM

(71) Applicant: Kookmin University Industry Academy Cooperation Foundation, Seoul (KR)

(72) Inventors: Si-Hyung Lim, Seoul (KR); Janghyeon Lee, Seoul (KR)

(73) Assignee: Kookmin University Industry Academy Cooperation Fo, Seoul (KR)

( * ) Notice: Subject to any disclaimer, the term of this patent is extended or adjusted under 35 U.S.C. 154(b) by 0 days.

(21) Appl. No.: 14/931,666

(22) Filed: Nov. 3, 2015

(65) Prior Publication Data

US 2016/0120442 A1 May 5, 2016

(30) Foreign Application Priority Data

Nov. 3, 2014 (KR) .................. 10-2014-0151306
Nov. 2, 2015 (KR) .................. 10-2015-0153085

(51) Int. Cl.

| A61B 5/083 | (2006.01) |
|---|---|
| B01D 53/02 | (2006.01) |
| A61B 5/097 | (2006.01) |
| B01J 20/20 | (2006.01) |
| B01J 20/28 | (2006.01) |
| A61B 5/08 | (2006.01) |
| B01D 53/04 | (2006.01) |

(52) U.S. Cl.
CPC .............. *A61B 5/097* (2013.01); *A61B 5/082* (2013.01); *B01D 53/0462* (2013.01); *B01J 20/20* (2013.01); *B01J 20/28014* (2013.01); *B01D 2253/102* (2013.01); *B01D 2253/25* (2013.01); *B01D 2253/304* (2013.01); *B01D 2257/708* (2013.01); *B01D 2259/4533* (2013.01)

(58) Field of Classification Search
CPC .... A61B 5/082; A61B 5/097; B01D 53/0407; B01D 2253/102; B01D 2257/404; B01D 2257/502; B01D 2257/708; B01D 2259/4533; B01J 20/20; B01J 20/28014
USPC ...... 96/108, 143, 146, 413; 95/90, 141, 148; 73/23.3, 31.02, 31.03, 863.11, 863.12, 73/864; 502/416; 422/88
See application file for complete search history.

(56) References Cited

U.S. PATENT DOCUMENTS

| 6,030,698 A * | 2/2000 | Burchell ................ B01D 53/02 428/293.4 |
|---|---|---|
| 6,171,378 B1 * | 1/2001 | Manginell .............. G01N 30/12 55/DIG. 5 |
| 6,527,835 B1 * | 3/2003 | Manginell ............. G01F 1/6845 55/524 |

(Continued)

FOREIGN PATENT DOCUMENTS

JP       2004-233061 A       8/2004

*Primary Examiner* — Frank Lawrence
(74) *Attorney, Agent, or Firm* — Knobbe Martens Olson & Bear LLP

(57) ABSTRACT

A gas concentration apparatus and a method of operating the gas concentration apparatus are provided. The gas concentration apparatus includes a gas concentration module. The gas concentration module includes a base component having a chamber configured to accommodate carbon foam, a gas inlet connected to one side of the chamber, a gas outlet connected to the other side of the chamber, and a heating device disposed on at least one side of the substrate.

17 Claims, 9 Drawing Sheets

(56) References Cited

U.S. PATENT DOCUMENTS

| | | | | |
|---|---|---|---|---|
| 7,422,724 B1* | 9/2008 | Manginell | ............ | B01J 20/3483 |
| | | | | 422/420 |
| 2007/0151326 A1* | 7/2007 | Kim | ..................... | G01N 1/2273 |
| | | | | 73/31.02 |
| 2008/0302246 A1* | 12/2008 | Carruthers | ......... | B01D 53/0415 |
| | | | | 96/154 |
| 2013/0253360 A1* | 9/2013 | Wang | ................. | G01N 33/0047 |
| | | | | 600/532 |
| 2014/0165705 A1* | 6/2014 | Li | ........................... | G01N 1/44 |
| | | | | 73/31.03 |

* cited by examiner

[FIG. 1]
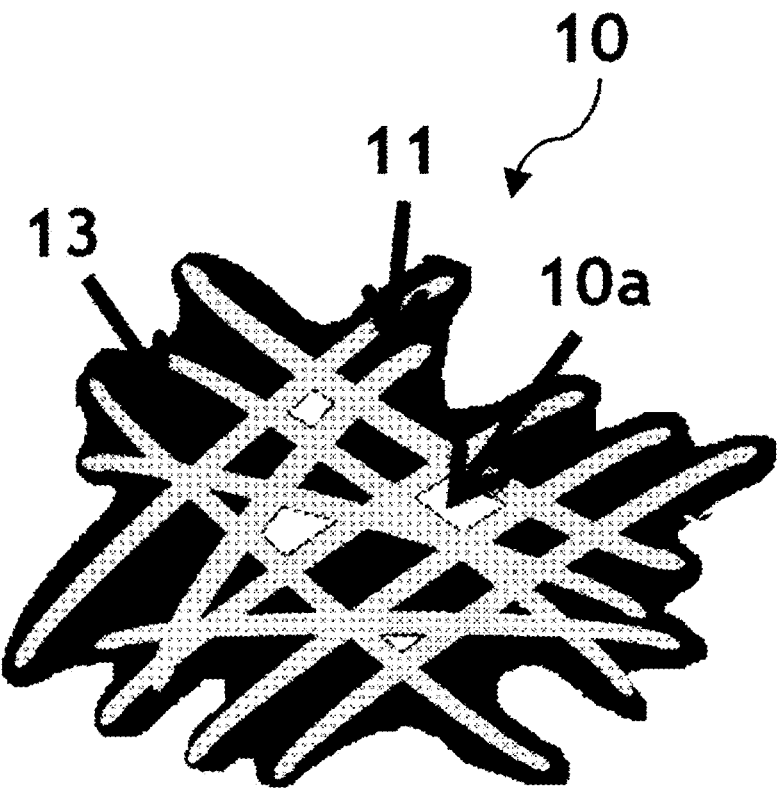
[FIG. 2]
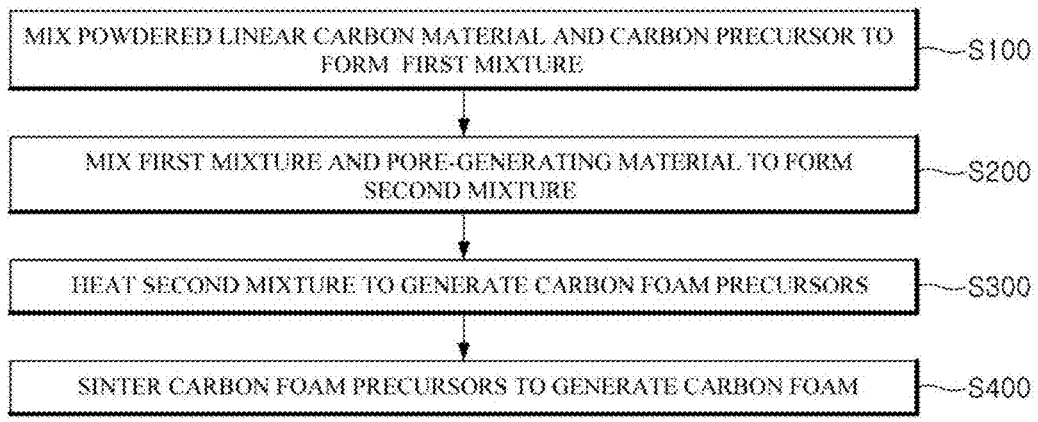

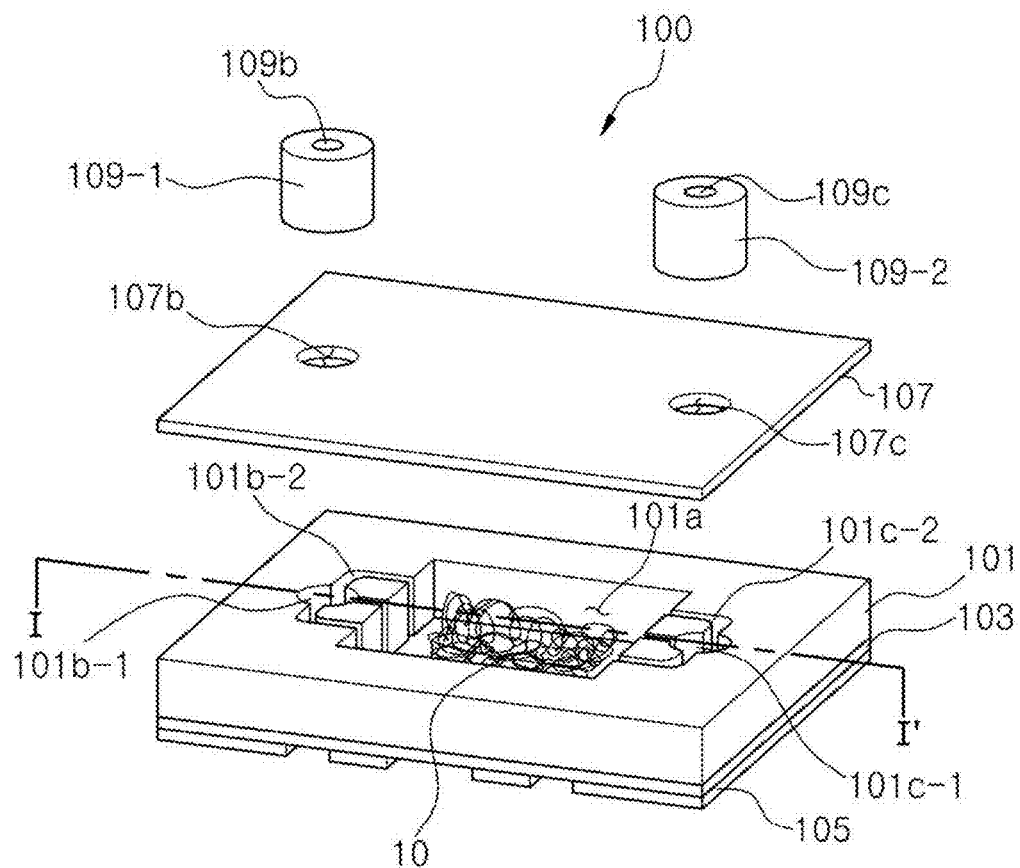
[FIG. 3A]
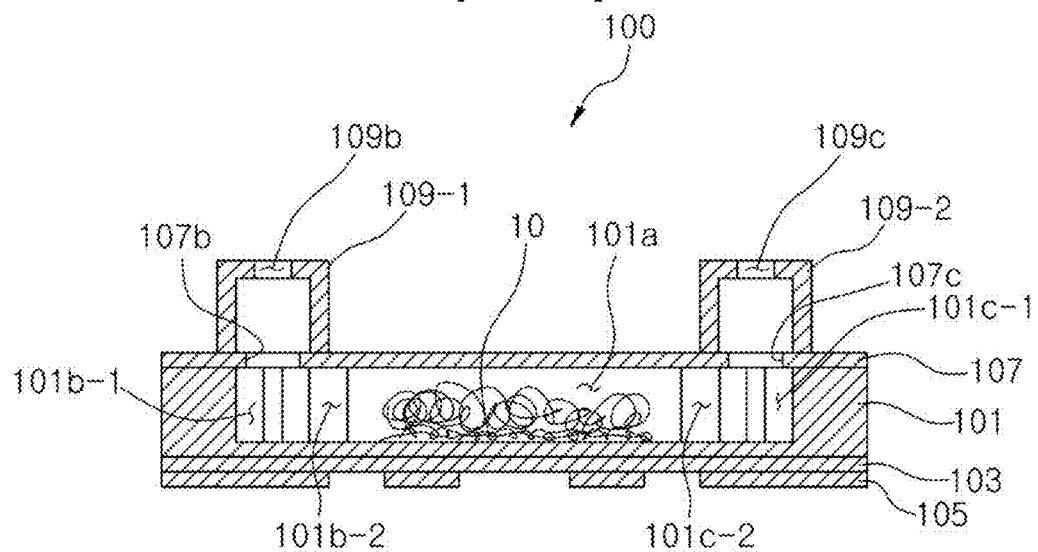
[FIG. 3B]

[FIG. 4]
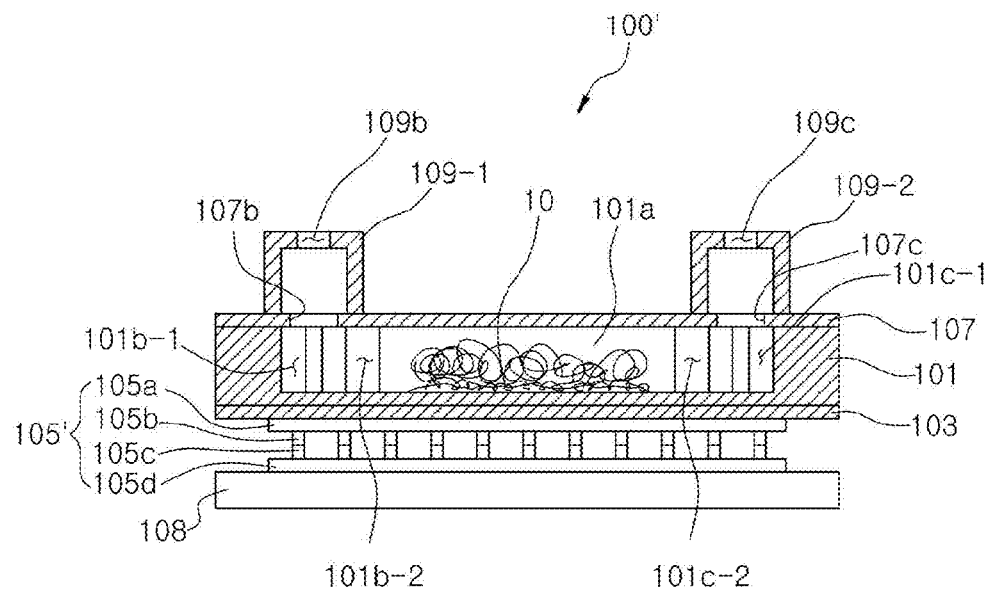
[FIG. 5]
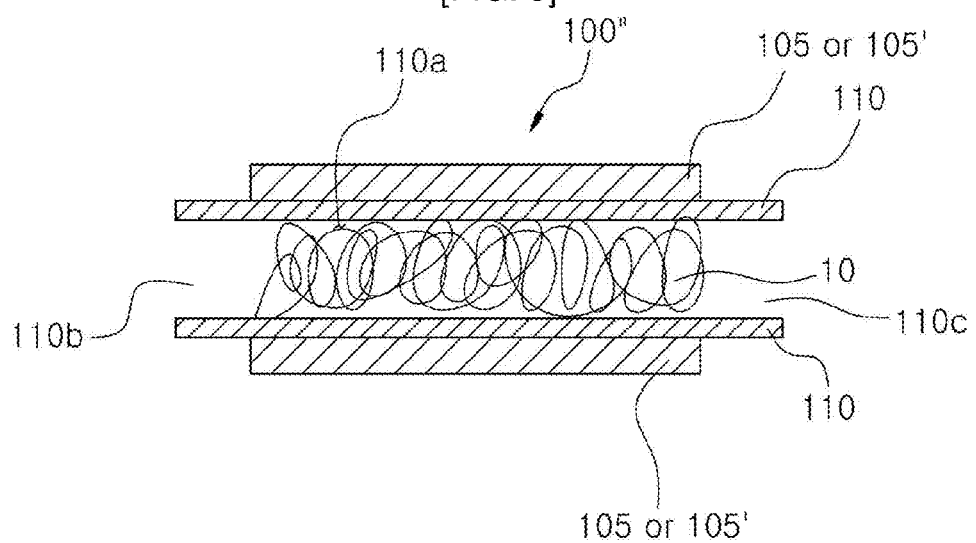

[FIG. 6]
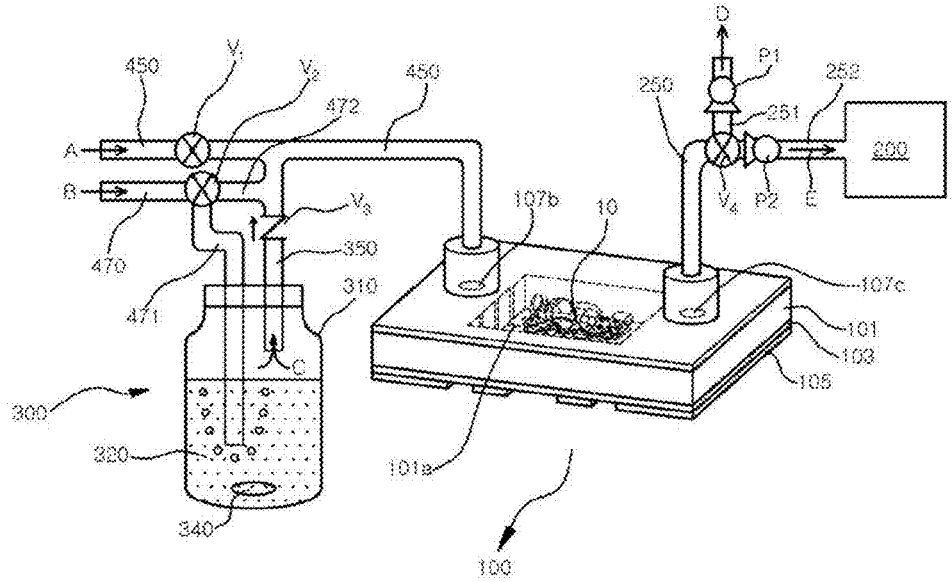
[FIG. 7]
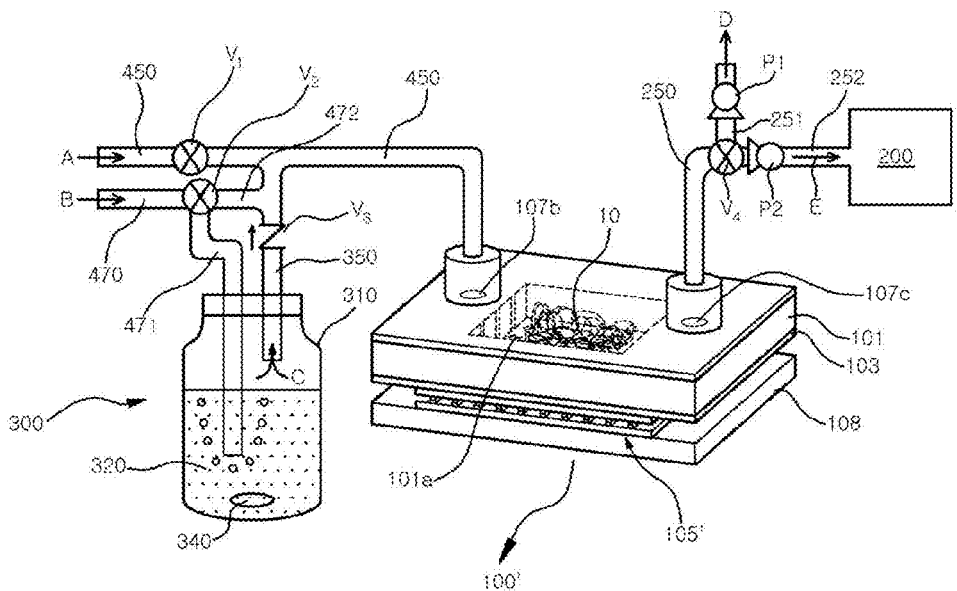

[FIG. 8]
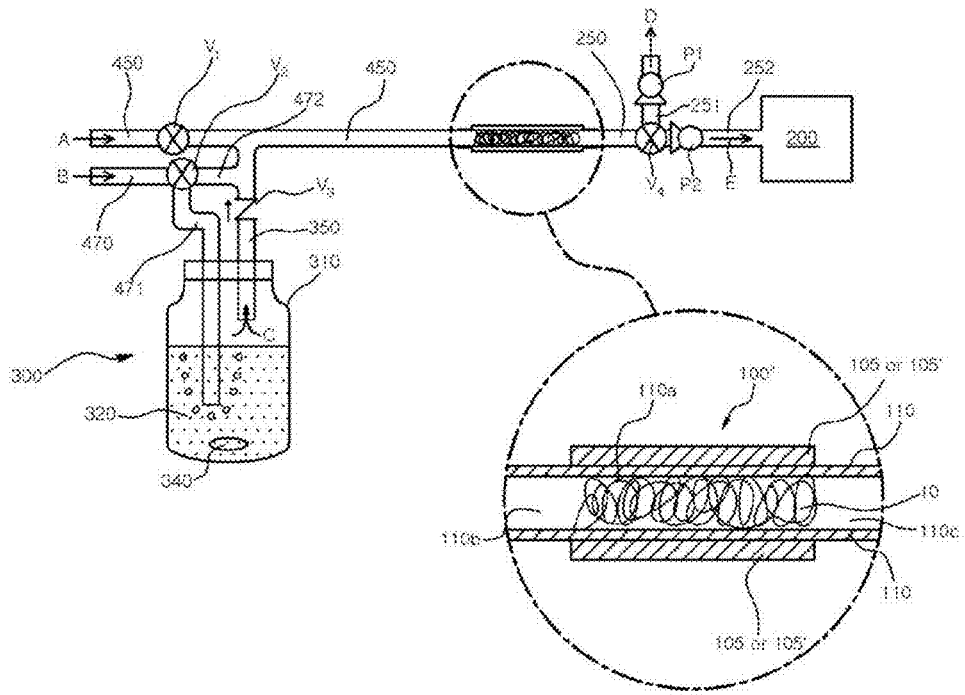
[FIG. 9A]
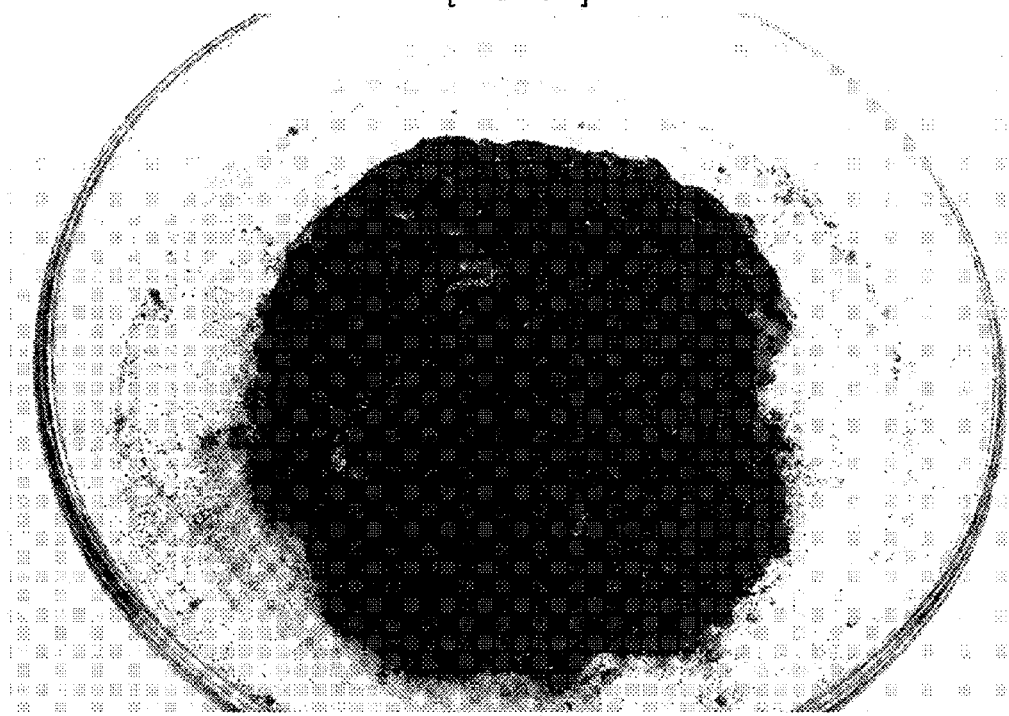

[FIG. 9B]
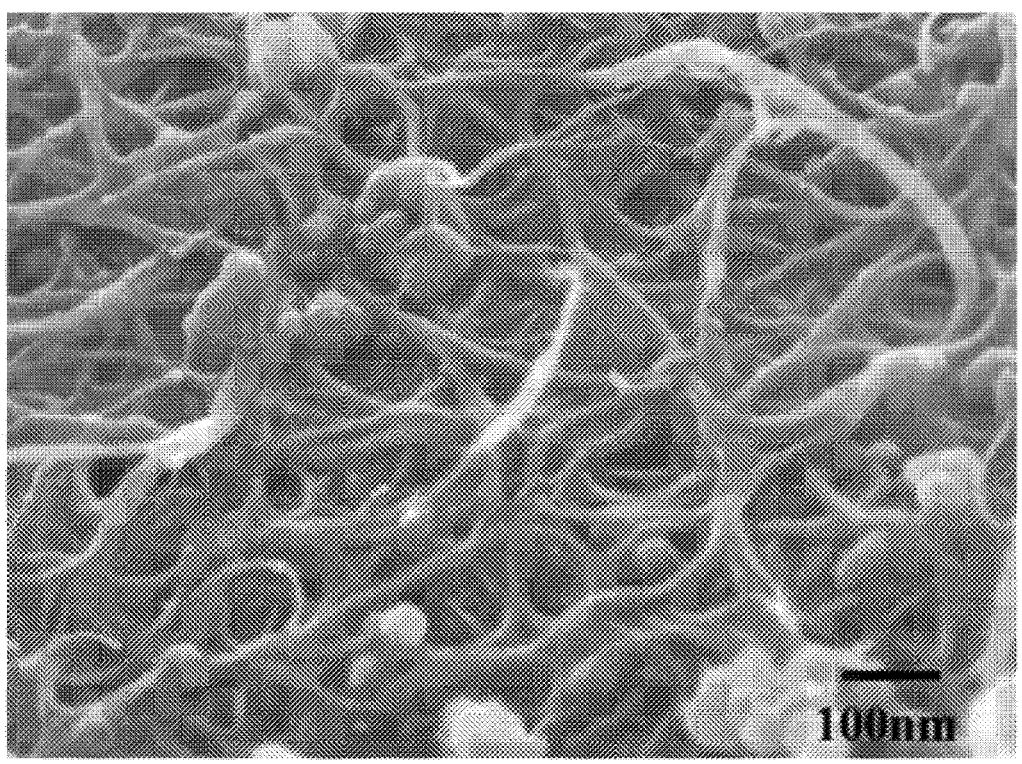

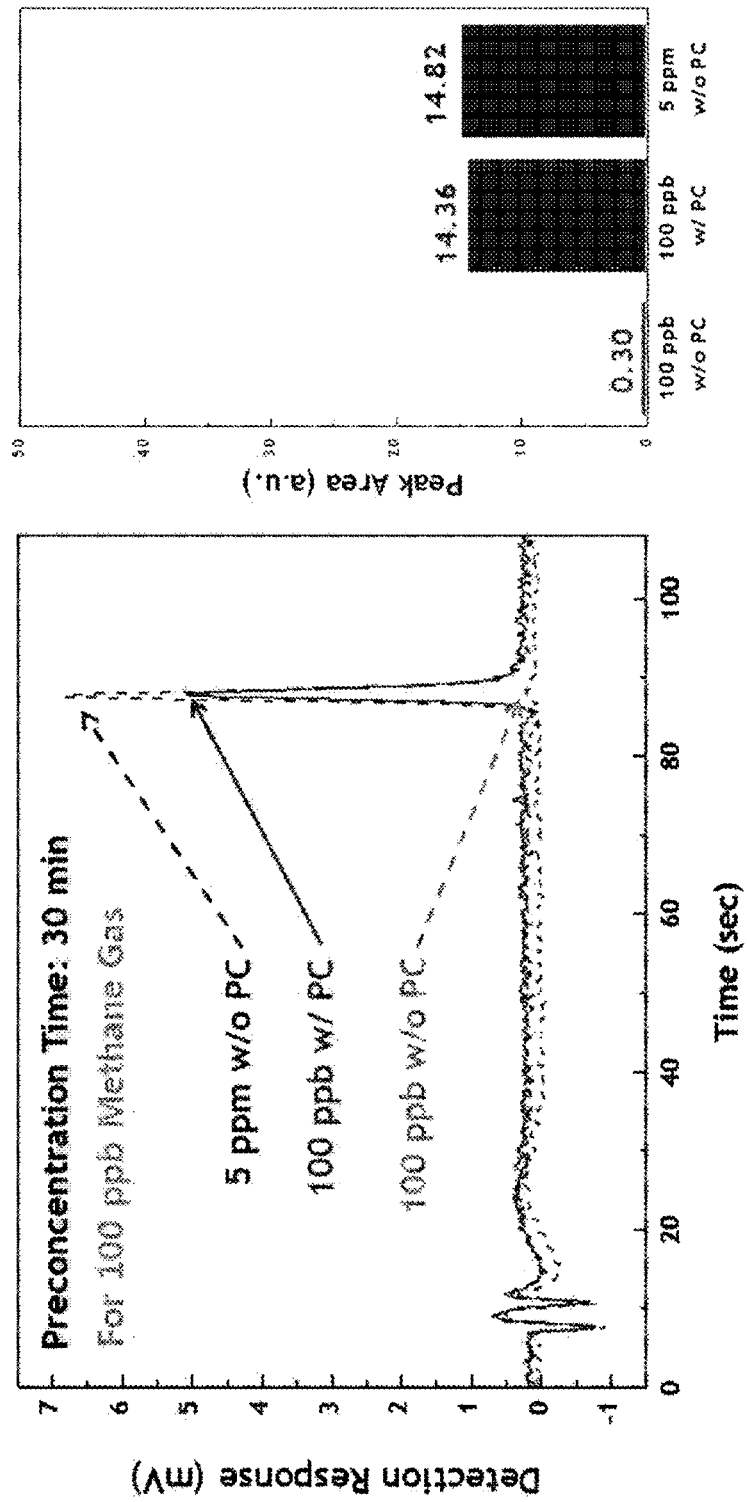

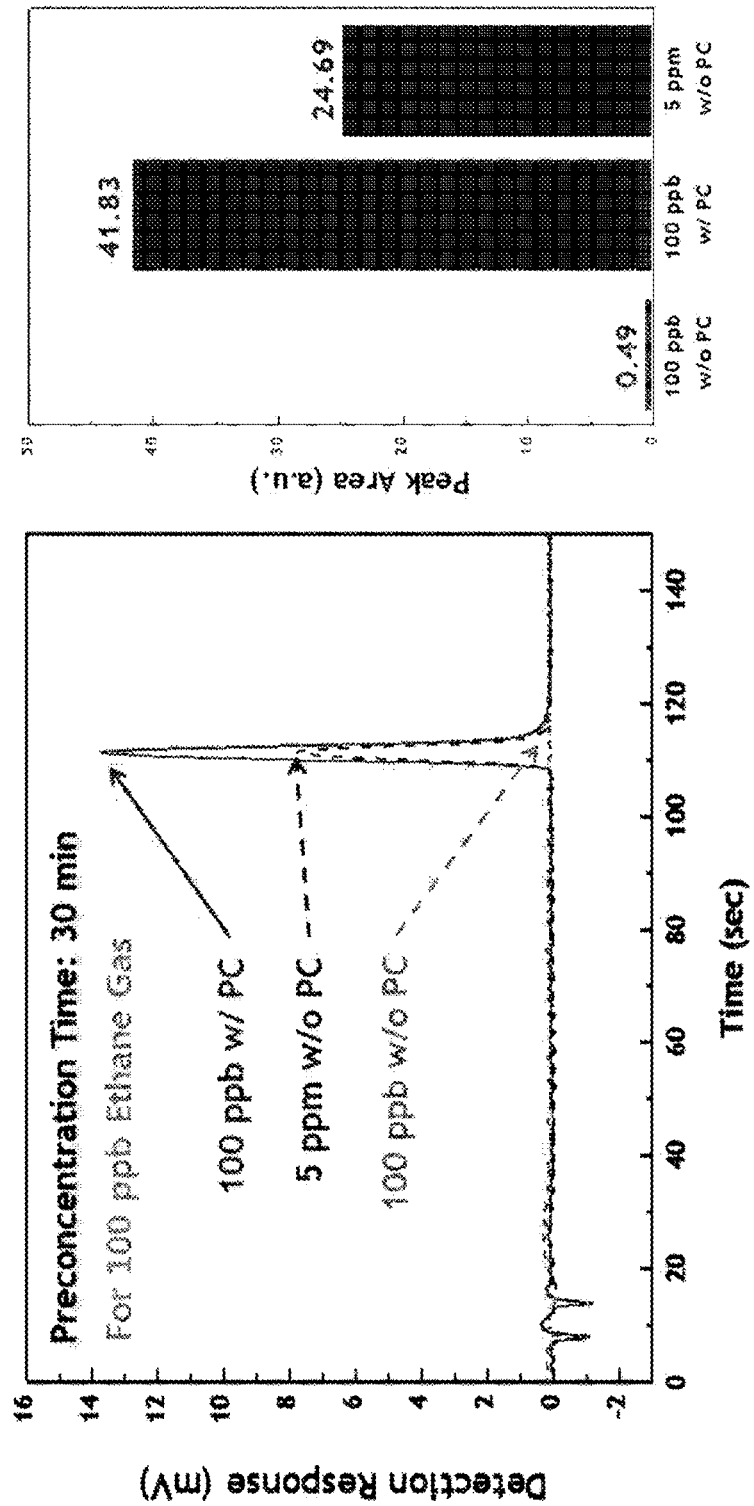

[FIG. 11]
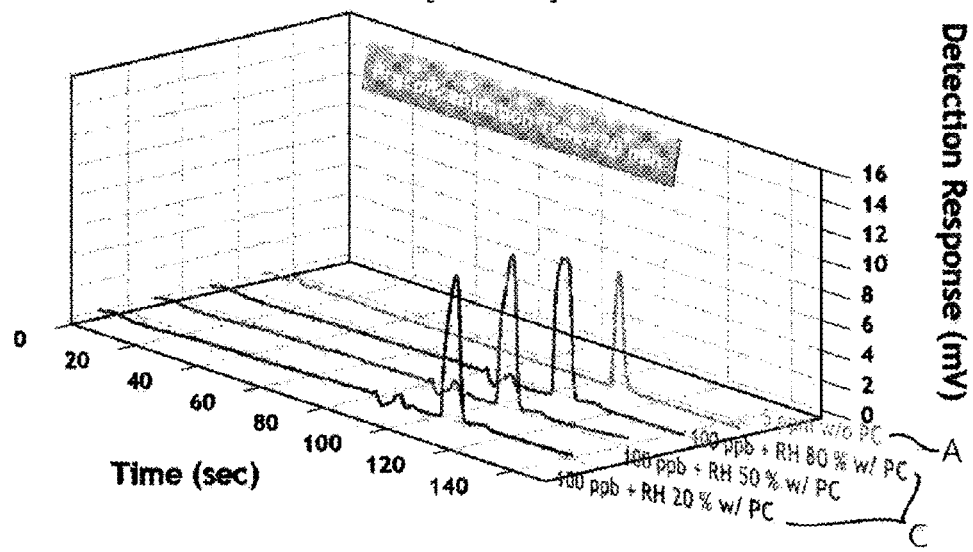
[FIG. 12]
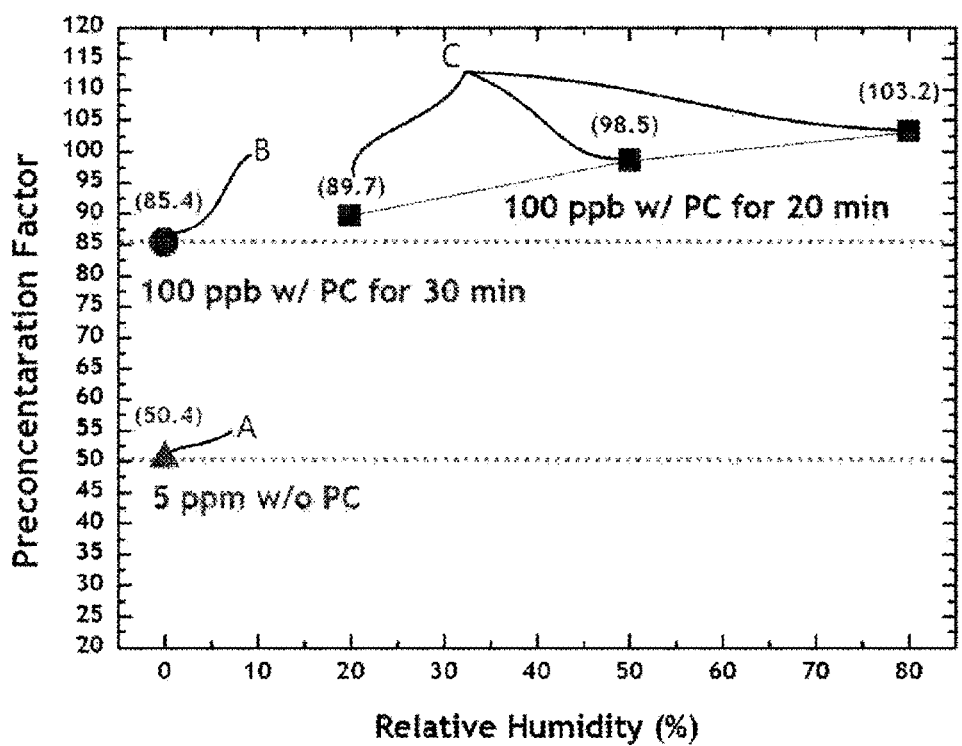

GAS CONCENTRATION APPARATUS HAVING CARBON FOAM

CROSS-REFERENCE TO RELATED APPLICATION

This application claims priority to and the benefit of Korean Patent Applications No. 10-2014-0151306, filed on Nov. 3, 2014 and No. 10-2015-0153085, filed on Nov. 2, 2015, the disclosure of which is incorporated herein by reference in its entirety.

BACKGROUND

1. Field

The present disclosure relates to a gas concentration apparatus and, more specifically, to a volatile organic compound gas concentration apparatus.

2. Discussion of Related Technology

Volatile organic compounds refer to liquid or gaseous organic compounds which have high vapor pressures and thus easily evaporate into the atmosphere. Such volatile organic compounds are known as air pollutants and toxic compounds having carcinogenicity.

In addition, it is known that a human respiratory gas, that is, an exhaled breath gas includes about 1000 types of compounds including volatile organic compounds at a considerably low concentration. Accordingly, when a specific compound among those compounds is detected as a biomarker, a condition and a disease of a patient may be predicted.

SUMMARY

An aspect of the present invention is directed to a gas concentration apparatus, which 1) reduces a pressure drop in a gas concentration process, 2) improves concentration efficiency, and/or 3) improves desorption efficiency after a gas absorption process.

Another aspect of the present invention provides a gas concentration apparatus. The gas concentration apparatus comprises a gas concentration module. The gas concentration module includes a base component including a chamber configured to accommodate carbon foam having linear carbon materials. A gas inlet is connected to one side of the chamber. A gas outlet connected to the other side of the chamber. A heating device disposed on at least one side of the base component.

The linear carbon materials may be irregularly arranged, and the carbon foam may further comprise a calcinated carbon layer coating outer surfaces of the linear carbon materials and a plurality of pores disposed between the linear carbon materials coated with the calcinated carbon layer.

The heating device may be a heater pattern or a peltier device. The base component may be a plate-type substrate, the chamber may be formed in a trench shape in an upper surface of the substrate, and the gas inlet and the gas outlet may be formed in a top plate covering the substrate. A source gas injecting through the gas inlet may include a volatile organic compound.

A source gas injection line may be connected to the gas inlet of the gas concentration module; and a droplet generation module may be connected to the source gas injection line. The droplet generation module may comprise a liquid storage unit configured to store a liquid, a droplet generator configured to generate droplets from the liquid storage unit, and a droplet discharge line connected to the source gas injection line. The liquid may contain water. The droplet generator may be a bubble-generating gas injection line or an ultrasonic vibrator immersed in the liquid.

Still another aspect of the present invention provides a method of operating a gas concentration apparatus. The method includes providing a gas concentration module including a base component having a chamber configured to accommodate carbon foam containing linear carbon materials, a gas inlet connected to one side of the chamber, a gas outlet connected to the other side of the chamber, and a heating device disposed on at least one side of the base component. A source gas including a target gas is supplied through the gas inlet to concentrate the target gas in the carbon foam. The heating device is heated to discharge the target gas concentrated in the carbon foam.

The linear carbon materials may be irregularly arranged, and the carbon foam may comprise a calcinated carbon layer coating outer surfaces of the linear carbon materials and a plurality of pores disposed between the linear carbon materials coated with the calcinated carbon layer.

The target gas may be a volatile organic compound. The source gas may be an exhaled breath gas. The heating device may be a heater pattern or a peltier device. When the heating device is a peltier device, the lowering of the temperature of the inside of the chamber may include cooling the peltier device, and the peltier device may be heated while discharging the target gas concentrated in the carbon foam.

A relative humidity may be increased in the chamber before or while supplying the source gas. The increasing of the relative humidity in the chamber may include supplying droplets to the chamber. In addition, simultaneously or separately, a temperature of the inside of the chamber may be lowered to increase the relative humidity.

A further aspect of the present invention provides carbon foam for a gas concentration apparatus. The carbon foam comprises linear carbon materials irregularly arranged, a calcinated carbon layer coating outer surfaces of the linear carbon materials, and a plurality of pores disposed between the linear carbon materials coated with the calcinated carbon layer.

BRIEF DESCRIPTION OF THE DRAWINGS

The above and other subjects, features, and advantages of the present invention will become more apparent to those of ordinary skill in the art by describing in detail embodiments thereof with reference to the accompanying drawings, in which:

FIG. 1 is a schematic diagram illustrating carbon foam according to an embodiment of the present invention;

FIG. 2 is a flowchart illustrating a method of fabricating carbon foam according to an embodiment of the present invention;

FIG. 3A is an exploded perspective view illustrating a gas concentration module according to an embodiment of the present invention, and FIG. 3B is a cross-sectional view taken along line I-I' of FIG. 3A;

FIG. 4 is a cross-sectional view illustrating a gas concentration module according to another embodiment of the present invention;

FIG. 5 is a cross-sectional view illustrating a gas concentration module according to still another embodiment of the present invention;

FIG. 6 is a schematic diagram illustrating a gas detector including a gas concentration apparatus according to an embodiment of the present invention;

FIG. 7 is a schematic diagram illustrating a gas detector including a gas concentration apparatus according to another embodiment of the present invention;

FIG. 8 is a schematic diagram illustrating a gas detector including a gas concentration apparatus according to another embodiment of the present invention;

FIGS. 9A and 9B are respectively an optical photograph and an SEM photograph of carbon nanotube foam according to Fabrication Example 1;

FIGS. 10A and 10B shows graphs illustrating results of methane gas concentration and ethane gas concentration in a gas concentration module according to Performance Evaluation 2, respectively; and FIGS. 11 and 12 are graphs illustrating results of gas concentration in a gas concentration module according to Performance Evaluation 3.

DETAILED DESCRIPTION OF EMBODIMENTS

Embodiments of the present invention will be described in detail below with reference to the accompanying drawings. However, since the present invention is not limited to the embodiments disclosed hereinafter, the embodiments of the present invention can be implemented in various forms. It will be understood that when a layer is referred to as being "on" another layer or a substrate, the layer may be formed directly on the other layer or the substrate, or an intervening layer may exist between the layer and the other layer or the substrate.

The present invention is not limited to the embodiments and the accompanying drawings disclosed, and only defined by the scope of the appended claims. Accordingly, it will be apparent to those skilled in the art that various modifications, equivalents, and alternatives can be made to the described embodiments of the present invention without departing from the spirit or scope of the invention, and it is intended that the present invention is to cover all such modifications, equivalents, and alternatives. The same reference numbers will be used throughout this specification to refer to the same or like components.

Spatially relative terms, such as "upper portion," "lower portion," "upper surface," "lower surface," and the like may be described as illustrated in the drawings, unless described otherwise. In illustrating a layered structure in the accompanying drawings, a portion closer to a display surface on which an image is displayed is illustrated to be disposed at an upper side, and a portion opposite thereto is illustrated to be disposed at a lower side.

It will be understood that, although the terms "first," "second," "A," "B," etc. may be used herein to describe various elements, these elements should not be limited by these terms. These terms are only used to distinguish one element from another. Therefore, a first element, a first component, or a first section could be termed a second element, a second component, or a second section within the scope of the invention. The term "and/or" includes any and all combinations of one or more referents.

It will be understood that when an element or layer is referred to as being "connected to" or "coupled to" another element or layer, it can be connected or coupled to the other element or layer or intervening elements or layers may be present. In contrast, when an element is referred to as "directly connected to" or "directly coupled to" another element or layer, there are no intervening elements or layers present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Generally, since the volatile organic compounds exist at extremely low concentrations in the atmosphere or the exhaled breath gas, a gas detector needs to have a high level of sensitivity in order to detect such a low concentration of gas. Commercialized metal oxide sensors are known not to satisfy the required level of sensitivity.

Thus, gas may be concentrated before the gas flows into a gas detection module. However, there may be a pressure drop during the gas concentration process, a low concentration efficiency, and low desorption efficiency after a gas absorption process.

FIG. 1 is a schematic diagram illustrating carbon foam according to an embodiment of the present invention.

Referring to FIG. 1, carbon foam 10 may include irregularly disposed linear carbon materials 11, a calcinated carbon layer 13 coating the outer surface of the linear carbon materials 11, and a plurality of pores 10a.

The linear carbon materials 11 may be carbon nanotubes, carbon nanohorns, or carbon nanofibers. The carbon nanotubes may be single-wall carbon nanotubes, double-wall carbon nanotubes, or multi-wall carbon nanotubes with more than two walls. Preferably, the carbon nanotubes may be single-wall carbon nanotubes having a tube-type carbon-atomic monolayer film structure and easily adsorbing gas molecules. Among the linear carbon materials 11, a material having crystallinity, such as carbon nanotubes, has high thermal conductivity and a structurally large surface area reacting with a gas. Accordingly, gas concentration efficiency may be improved.

The calcinated carbon layer 13 is a layer formed by sintering carbon precursors, and may be in an amorphous state. The calcinated carbon layer 13 may adsorb a gas by Van der Waals attractions, and may serve to bind the linear carbon materials 11. A thickness of the calcinated carbon layer 13 may be in the range of several tens to several hundreds of nanometers.

The plurality of pores 10a may be disposed between adjacent linear carbon materials 11 coated by the calcinated carbon layer 13, or inside the calcinated carbon layer 13. Accordingly, a gas flow path may be sufficiently formed, and thus a pressure drop during the gas concentration process may be reduced. An average diameter of the pores 10a may be in the range of about 100 to 200 nm.

The carbon foam 10 may adsorb organic gas better than inorganic gas. In addition, the surface of the carbon foam 10 may be reformed in order to increase selectivity with respect to a target gas to be concentrated.

FIG. 2 is a flowchart illustrating a method of fabricating carbon foam according to an embodiment of the present invention.

Referring to FIG. 2, 100 parts by weight of powdered linear carbon materials and 300 to 700 parts by weight of carbon precursors may be mixed to form a first mixture (S100). The powdered linear carbon materials may be powdered carbon nanotubes, powdered carbon nanohorns, or powdered carbon nanofibers. More specifically, the powdered linear carbon materials may be powdered carbon nanotubes having a purity of 20 to 30% at room temperature. The carbon precursors may be dextrose and citric acid. More specifically, the carbon precursors may be 100 to 300 parts by weight of dextrose and 200 to 400 parts by weight of citric acid.

Next, the first mixture and 100 to 300 parts by weight of a pore-generating material may be mixed to form a uniform second mixture (S200). The pore-generating material may be ammonium carbonate.

The second mixture may be heated to generate carbon foam precursors (S300). More specifically, the second mixture may be heated at a temperature in the range of 110 to 150° C. for 3 to 7 hours. In this process, ammonium carbonate, the pore-generating material, may be decomposed to form pores.

Next, the carbon foam precursors may be sintered to form carbon foam (S400). More specifically, the carbon foam precursors may be sintered at a temperature in the range of 400 to 500° C. for 2 to 4 hours. In this process, the carbon precursors may be thermally decomposed and sintered to be changed into a calcinated carbon layer, which coats and binds the linear carbon materials, and may form additional pores.

FIG. 3A is an exploded perspective view illustrating a gas concentration module according to an embodiment of the present invention, and FIG. 3B is a cross-sectional view taken along line I-I' of FIG. 3A.

Referring to FIGS. 3A and 3B, a base component including a chamber 101a may be provided. The base component may be a plate-type substrate 101. More specifically, the chamber 101a may be formed in an upper surface of the substrate 101. The substrate 101 may be a silicon substrate, but is not limited thereto. The chamber 101a may be formed in a trench shape in the upper surface of the substrate 101 by etching the upper surface of the substrate 101. Together with the chamber 101a, a first suction path 101b-1 and a plurality of second suction paths 101b-2 connecting the first suction path 101b-1 to the chamber 101a may be formed at one side of the chamber 101a. In addition, a first discharge path 101c-1 and a plurality of second discharge paths 101c-2 connecting the first discharge path 101c-1 to the chamber 101a may be formed at the other side of the chamber 101a.

The chamber 101a may be a space for accommodating the carbon foam 10 described with reference to FIG. 1. The suction paths 101b-1 and 101b-2 may be paths through which a sample gas is sucked, and the discharge paths 101c-1 and 101c-2 may be paths through which a residual gas which is unabsorbed in the carbon foam 10, or a concentrated gas which is desorbed is discharged.

Before the chamber 101a is formed, an insulating layer 103 may be formed on a lower surface of the substrate 101. The insulating layer 103 may be a silicon oxide layer, a silicon nitride layer, or a multilayer thereof, but is not limited thereto. For example, the insulating layer 103 may be a double layer of a silicon oxide layer having compressive stress and a silicon nitride layer having tensile stress. The insulating layer 103 may be formed by thermal oxidation, sputtering, chemical mechanical deposition (CVD), or the like. A thickness of the insulating layer 103 may be in the range of 500 to 1500 nm, but is not limited thereto.

An insulating layer may also be formed on the upper surface of the substrate 101. The insulating layer formed on the upper surface of the substrate 101 may be used as a hardmask during an etching process for forming the chamber 101a.

A heating device may be disposed on the insulating layer 103 formed on the lower surface of the substrate 101. More specifically, the heating device may be a heater pattern 105. Here, the insulating layer 103 may serve to prevent deformation of the gas concentration module 100 caused by heat generated while the heater pattern 105 is heated.

The heater pattern 105 may include an adhesion layer for improving adhesion with the insulating layer 103, and a conductive layer disposed on the adhesion layer. The heater pattern 105 may be formed by a liftoff method or the like. The adhesion layer may be formed of various types of metal, such as Al, Pt, Cr, or Ti, or doped polysilicon. The conductive layer may be formed of one selected from the group consisting of Au, W, Pt, Pd, and any combinations thereof, but is not limited thereto. In addition, the heater pattern 105 may be formed by forming a thin film using sputtering, e-beam evaporation, or evaporation, and patterning the thin film using a photolithography and etching process, such as a liftoff process.

For example, the heater pattern 105 may be formed in the form of a successively overlapped heating wire like zigzag pattern. As another example, the heater pattern 105 may be formed in an inter-digital type.

In addition to the heater pattern 105, another thin film may be formed on the insulating layer 103 in order to increase stability of the gas concentration module 100, as needed. Meanwhile, a thickness of the substrate 101 may be adjusted by a mechanical polishing process or a chemical mechanical polishing (CMP) process.

The carbon foam 10 described with reference to FIG. 1 may be disposed in the chamber 101a. Here, a density of the carbon foam 10 may be appropriately set to further improve a gas adsorption capacity, a pressure drop, and the like. After the carbon foam 10 is disposed, a surface of the carbon foam 10 may be reformed according to an application of a gas to be adsorbed.

Next, a top plate 107 covering or sealing the chamber 101a may be disposed on the substrate 101. The top plate 107 may be coupled to the substrate 101 using thermal glue, but is not limited thereto. The top plate 107 may include an inlet 107b corresponding to the first suction path 101b-1, and an outlet 107c corresponding to the first discharge path 101c-1. In addition, a first connector 109-1 including an inlet through-hole 109b corresponding to the inlet 107b, and a second connector 109-2 including an outlet through-hole 109c corresponding to the outlet 107c may be formed on the top plate 107. A substrate formed of silicon or tempered glass may be used as the top plate 107. In addition, before the top plate 107 is coupled to the substrate 101, the top plate 107 may be machined using a deep reactive ion etching (DRIE) process or an ultrasonic machining process, to form the inlet 107b and the outlet 107c.

When the process of forming the gas concentration module 100 is performed in a wafer level process in which a plurality of modules are formed at the same time, a process of cutting each module may be additionally performed after the gas concentration module is completed.

FIG. 4 is a cross-sectional view illustrating a gas concentration module according to another embodiment of the present invention. The gas concentration module according to the embodiment of the present invention may be similar to the gas concentration module described with reference to FIGS. 3A and 3B, except the explanation to be described below.

Referring to FIG. 4, an insulating layer 103 may be formed on a lower surface of a substrate 101 including a chamber 101a in a surface thereof. A heating device may be disposed on the insulating layer 103. The heating device may be a peltier device 105'. The peltier device 105' may include a first conductive layer 105a, a first-type semiconductor layer 105b, a second-type semiconductor layer 105c, and a second conductive layer 105d. One of the first-type semiconductor layer 105b and the second-type semiconductor layer 105c may be an n-type semiconductor layer, and the other one may be a p-type semiconductor layer. In addition, a heat sink 108 may be disposed below the peltier device 105'. In the peltier device 105', the first conductive layer 105a may be heated while the second conductive layer 105d is cooled, or the first conductive layer 105a may be cooled while the second conductive layer 105d is heated, depending on a direction of currents flowing through a junction between the first-type semiconductor layer 105b and the second-type semiconductor layer 105c. Accordingly, a module 100' including the peltier device 105' may be heated or cooled, as needed. Meanwhile, the heat sink 108 has excellent heat transfer characteristics and may serve to transfer heat from the outside to the peltier device 105' or from the peltier device 105' to the outside. Accordingly, cooling or heating efficiency of the module 100' may be improved.

FIG. 5 is a cross-sectional view illustrating a gas concentration module according to still another embodiment of the present invention.

Referring to FIG. 5, a chamber 110a accommodating the carbon foam 10 described with reference to FIG. 1, a substrate including a suction path or inlet 110b connected to one side of the chamber 110a, and a discharge path or outlet 110c connected to the other side of the chamber 110a, may be provided. The substrate may be a tube 110. For example, the tube 110 may be a metal, glass, or plastic tube. More specifically, when the tube 110 is a glass or plastic tube, the tube 110 may be tempered glass or tempered plastic, which is not deformed within the range of an operating temperature of a gas concentration module 100". In addition, when the tube 110 is a metal tube, an outer surface of the metal tube may be coated with an insulating layer.

The chamber 110a, that is, the inside of the tube 110 may be filled with the carbon foam 10. Here, a filling degree of the carbon foam 10 may be appropriately set to further improve a gas adsorption capacity, a pressure drop, or the like.

A heating device may be disposed below, on top and below, or around the tube 110. The heating device may be the heater pattern 105 described with reference to FIGS. 3A and 3B or the peltier device 105', which is selectively heated or cooled, described with reference to FIG. 4. When the heating device is the peltier device 105', the heating device may be disposed below, or on top and below the tube 110 in a plate form.

FIG. 6 is a schematic diagram illustrating a gas detector including a gas concentration apparatus according to an embodiment of the present invention.

Referring to FIG. 6, the gas detector may include a gas concentration apparatus and a gas detection module 200. The gas concentration apparatus may include the gas concentration module 100 described with reference to FIGS. 3A and 3B and a droplet generation module 300 connected to the inlet 107b of the gas concentration module 100. The gas detection module 200 may be connected to the outlet 107c of the gas concentration module 100.

The droplet generation module 300 supplies micro-droplets to the carbon foam 10 through the inlet 107b of the gas concentration module 100, and may include a liquid storage part 310 storing a liquid 320, a droplet generator generating droplets from the liquid storage part 310, such as a sprayer, a heater, an ultrasonic vibrator 340, or a bubble-generating gas injection line 471 immersed in the liquid 320, and a droplet discharge line 350 connected to the inlet 107b of the gas concentration module 100. The liquid 320 may include water, and the micro-droplets may have a diameter in the range of several to several tens of micrometers.

Meanwhile, a source gas injection line 450 to which a source gas A containing a target gas or a diagnostic marker is injected, may be connected to the inlet 107b of the gas concentration module 100. A first valve $V_1$ controlling the amount of the source gas to be injected may be disposed in the source gas injection line 450. A carrier gas injection line 470 may be connected to the source gas injection line 450. The bubble-generating gas injection line 471 and a carrier gas transfer line 472 may be divided from the carrier gas injection line 470. In the division point, a second valve $V_2$, for example, a three-way valve such as a three-way solenoid valve may be disposed. The carrier gas transfer line 472 and the droplet discharge line 350 may be connected to the source gas injection line 450 and thus connected to inlet 107b of the gas concentration module 100. A third valve $V_3$ capable of opening and shutting the flow of the micro-droplets, may be disposed in the droplet discharge line 350. The third valve $V_3$ may be a check valve allowing fluid to flow through it in only one direction.

Meanwhile, the gas detection module 200 detects a type of a concentrated target gas discharged from the outlet 107c of the gas concentration module 100, and may be a gas sensor, a gas chromatography device, a mass spectrometry device, a Fourier transform infrared spectrometry (FTIR) device, or an ion mobility spectrometry device. More specifically, a gas discharge line 250 may be connected to the outlet 107c of the gas concentration module 100. The gas discharge line 250 may be divided into an external discharge line 251 connected to the outside and a gas detection line 252 connected to the gas detection module 200. In the division point, a fourth valve $V_4$, for example, a three-way valve such as a three-way solenoid valve may be disposed. In addition, pumps P1 and P2 may be disposed in both the external discharge line 251 and the gas detection line 252. The pumps P1 and P2 may be micro-pumps known to be capable of transferring an extremely small amount of fluid applicable to a micro-sized synthetic chemical analyzer, a lap-on-a-chip, or the like, required for high-tech medical fields, chemical fields, and biotechnology. However, the pumps P1 and P2 are not limited to a specific mode of operation as long as the pumps P1 and P2 control a constant amount of fluid to be supplied. The pumps P1 and P2 may not only suction the gas, but also function to control the amount of gas to be suctioned.

A method of operating a gas concentration apparatus in accordance with an embodiment of the inventive concept will be described with reference again to FIG. 6.

Gas Concentration Process

The first valve $V_1$ is opened and a source gas A containing a target gas is injected through the source gas injection line 450. The source gas A may be a gas including a volatile organic compound, and more specifically, an exhaled breath gas, containing a diagnostic marker, of a patient. For example, the source gas A may be an exhaled breath gas, containing methane and/or ethane, of a patient suffering from gut bacteria, breast cancer, lipid peroxidation, irritable bowel syndrome, or colon cancer. As another example, the source gas A may be an exhaled breath gas of a patient suffering from asthma, chronic obstructive pulmonary disease (COPD), or a variety of other respiratory diseases, and may contain a diagnostic marker, such as carbon monoxide (CO), nitrogen monoxide (NO), and/or a plurality of alkane compounds.

While the source gas A is injected, the bubble-generating gas injection line 471 is opened by the second valve $V_2$ to flow a carrier gas B into the droplet generation module 300 through the bubble-generating gas injection line 471. The carrier gas B may be an inert gas such as nitrogen, or dry air. The carrier gas B flowing into a liquid 320 in the droplet generation module 300 may generate bubbles in the liquid 320. Simultaneously or separately, the vibrator 340 in the droplet generation module 300 may be operated. As a result, micro-droplets C may be collected above the liquid 320 in the droplet generation module 300. At this time, the third valve $V_3$ is opened so that the micro-droplets are discharged through the droplet discharge line 350, then flow into the source gas injection line 450, and then flow into the inlet 107*b* of the gas concentration module 100, together with the source gas.

In this case, a target gas in the source gas may be adsorbed and concentrated in the carbon foam 10 in the gas concentration module 100. Here, the micro-droplets supplied with the source gas may firstly adsorb the target gas molecules and also increase a relative humidity in the chamber 101*a*. The micro-droplets with the target gas molecules may be secondarily adsorbed in the carbon foam 10. In addition, the target gas molecules not adsorbed in the micro-droplets can be easily adsorbed in the carbon foam 10 by the increased relative humidity in the chamber 101*a*. As a result, an adsorption rate of the target gas into the carbon foam 10 may be improved. Accordingly, the degree of concentration of the target gas in the carbon foam 10 may increase and, at the same time, concentration time may decrease. Here, the heater pattern 105 of the gas concentration module 100 may not be heated since currents are not supplied thereto, and accordingly the carbon foam 10 in the chamber 101*a* may be in a room temperature state.

Meanwhile, a residual gas D which is not adsorbed to the carbon foam 10 may be discharged through the outlet 107*c* of the gas concentration module 100. Here, the external discharge line 251 is opened by the fourth valve $V_4$, and at the same time, the gas detection line 252 is closed to discharge the residual gas D discharged through the outlet 107*c* of the gas concentration module. Here, a pump P1 disposed in the external discharge line 251 may be operated to control the flow of gas.

Gas Description Process

When a predetermined time is passed and the target gas is sufficiently concentrated in the carbon foam 10 in the gas concentration module 100, the heater pattern 105 of the gas concentration module 100 is turned on, so as to induce the heater pattern 105 to generate heat. As a result, the target gas concentrated in the carbon foam 10 in the gas concentration module 100 may start to be discharged. Here, since the linear carbon materials of the carbon foam 10, such as carbon nanotubes, have excellent heat transfer characteristics, discharge efficiency of the target gas may be further improved and discharge time may be shortened.

Here, the carrier gas B may flow into the gas concentration module 100 via the carrier gas transfer line 472 and the source gas injection line 450 by closing the first valve $V_1$ disposed in the source gas injection line 450 and the third valve $V_3$ disposed in the droplet discharge line 350, and closing the bubble-generating gas injection line 471 and opening the carrier gas transfer line 472 at the same time using the second valve $V_2$ disposed in the carrier gas injection line 470. In addition, by closing the external discharge line 251 and opening the gas detection line 252 at the same time using the fourth valve $V_4$, a target gas E discharged through the outlet 107*c* of the gas concentration module may be supplied to the gas detection module 200 via the gas detection line 252. Here, a pump P2 disposed in the gas detection line 252 may be operated to control the flow of the gas.

In this manner, since the concentration of the target gas E supplied to the gas detection module 200 is significantly improved compared to the concentration of the target gas E in the source gas A, detection performance of the gas detection module 200 may be significantly improved.

FIG. 7 is a schematic diagram illustrating a gas detector including a gas concentration apparatus according to another embodiment of the present invention. The gas detector according to the embodiment of the present invention may be similar to the gas detector described with reference to FIG. 6, except the explanation to be described below.

Referring to FIG. 7, the gas detector may include a gas concentration apparatus and a gas detection module 200. The gas concentration apparatus may include the gas concentration module 100' described with reference to FIG. 4 and a droplet generation module 300 connected to the inlet 107*b* of the gas concentration module 100'. The gas detection module 200 may be connected to the outlet 107*c* of the gas concentration module 100'.

In the gas concentration process, simultaneously with supplying micro-droplets to the chamber 101*a* using the droplet generation module 300, or separately, the peltier device 105' included in the gas concentration module 100' may be operated to cool down the first conductive layer (reference numeral 105*a* in FIG. 4) disposed adjacent to the chamber 101*a*, and thus may lower the temperature of the chamber 101*a* (a cooling operation). In embodiments, the temperature in the chamber 101*a* may be lower than room temperature. For example, the temperature in the chamber 101*a* may be in the range of −10 to 10° C. In this case, the relative humidity in the chamber 101*a* may be further increased. Accordingly, the adsorption rate of a target gas into the carbon foam 10 and the degree of concentration of the target gas in the carbon foam 10 may be improved.

Meanwhile, in the gas desorption process, the peltier device 105' may be operated to heat the first conductive layer (reference numeral 105*a* in FIG. 4) disposed to be adjacent to the chamber 101*a*, and thus may increase the temperature of the chamber 101*a* (a heating operation). As a result, the concentrated target gas in the carbon foam 10 in the gas concentration module 100 may start to be discharged.

In the gas concentration process and the gas desorption process, since the linear carbon materials of the carbon foam 10, such as carbon nanotubes, have high heat transfer characteristics, concentration efficiency and discharge efficiency of the target gas may further be improved.

FIG. 8 is a schematic diagram illustrating a gas detector including a gas concentration apparatus according to another embodiment of the present invention. The gas detector according to the embodiment of the present invention may be similar to the gas detector described with reference to FIG. 6 or FIG. 7, except the explanation to be described below.

Referring to FIG. 8, the gas detector may include the gas concentration apparatus and the gas detection module 200. The gas concentration apparatus may include the gas concentration module 100" described with reference to FIG. 5 and a droplet generation module 300 connected to the inlet 110b of the gas concentration module 100". The gas detection module 200 may be connected to the outlet 110c of the gas concentration module 100".

When a heating device included in the gas concentration module 100" is the heater pattern 105, the heating device may be operated as described with reference to FIG. 6, and when the heating device included in the gas concentration module 100" is the peltier device 105', the heating device may be operated as described with reference to FIG. 7.

Hereinafter, experimental examples will be provided for a better understanding of the present invention. However, the present invention should not be construed as limited to the experimental examples.

<Fabrication Example 1 of Carbon Nanotube Foam>

A first mixture was formed by mixing 500 mg (200 parts by weight) of dextrose and 700 mg (280 parts by weight) of citric acid to 250 mg (100 parts by weight) of powdered carbon nanotubes having 25% purity at room temperature, and 500 mg (200 parts by weight) of ammonium carbonate was uniformly mixed with the first mixture. Next, the mixture was heated at a temperature of 130° C. for 5 hours to form carbon nanotube foam precursors. The carbon nanotube foam precursors were thermally decomposed at a temperature of 450° C. for 3 hours to remove organic materials and form carbon nanotube foam.

<Fabrication Example 2 of Carbon Nanotube Foam>

Carbon nanotube foam was fabricated using the same method as that described in Fabrication Example 1, except that 1 g (100 parts by weight) of powered carbon nanotubes, 4 g (400 parts by weight) of dextrose, 6 g (600 parts by weight) of citric acid, and 2 g (200 parts by weight) of ammonium carbonate were used.

<Fabrication Example 3 of Carbon Nanotube Foam>

Carbon nanotube foam was fabricated using the same method as that described in Fabrication Example 1, except that 500 mg (100 parts by weight) of powered carbon nanotubes, 1 g (200 parts by weight) of dextrose, 2 g (400 parts by weight) of citric acid, and 1 g (200 parts by weight) of ammonium carbonate were used and the carbon nanotube foam precursors were thermally decomposed at a temperature of 300° C.

FIGS. 9A and 9B are respectively an optical photograph and an SEM image of the carbon nanotube foam according to Fabrication Example 1.

Referring to FIGS. 9A and 9B, the carbon nanotubes are covered by an amorphous carbon layer, and a plurality of pores exist therebetween.

<Performance Evaluation 1 of Gas Concentration Module>

The carbon nanotube foam obtained by Fabrication Example 1 was disposed in the chamber of the gas concentration module described with reference to FIGS. 3A and 3B, and degrees of pressure drop were measured while flowing the source gas at 100 sccm, 200 sccm, 300 sccm, and 400 sccm.

In the pressure drop test for the carbon nanotube foam obtained by Fabrication Example 1, when the source gas flowed at 100 sccm, 200 sccm, 300 sccm, and 400 sccm, the pressure drop values were respectively 81 Pa, 222 Pa, 446 Pa, and 621 Pa, which are extremely satisfactory.

<Performance Evaluation 2 of Gas Concentration Module>

The carbon nanotube foam obtained by the fabrication examples was disposed in the chamber of the gas concentration module described with reference to FIGS. 3A and 3B, and a concentration performance test (GC-FID analysis) on methane and ethane was executed.

FIGS. 10A and 10B shows graphs illustrating results of methane gas concentration and ethane gas concentration in a gas concentration module according to Performance Evaluation 2, respectively. Here, the carbon nanotube foam obtained by Fabrication Example 1 was used.

Referring to FIG. 10A, when flowing a source gas containing 100 ppb of methane into the gas concentration module at a flow rate of 150 sccm for about 30 minutes, then increasing a temperature of the chamber of the gas concentration module to about 300° C. for 2 minutes using a heater pattern, and detecting a discharged gas from the chamber (100 ppb w/ PC), an integrated area of a reaction peak was 14.36 mV·s. When detecting the source gas without using the gas concentration module (100 ppb w/o PC), the integrated area of a reaction peak was 0.3 mV·s. Accordingly, a preconcentration factor was 47.9 when the gas concentration module was used.

In addition, the integrated area of the reaction peak which is 14.36 mV·s when detecting the gas after concentrating the source gas containing 100 ppb methane using the gas concentration module (100 ppb w/ PC) is almost the same as the integrated area of the reaction peak which is 14.82 mV·s when detecting the source gas containing 5 ppm methane without using the gas concentration module (5 ppm w/o PC).

Referring to FIG. 10B, when flowing a source gas containing 100 ppb of ethane into the gas concentration module at a flow rate of 150 sccm for about 30 minutes, then increasing a temperature of the chamber of the gas concentration module to about 300° C. for 2 minutes using a heater pattern, and detecting a discharged gas from the chamber (100 ppb w/ PC), an integrated area of a reaction peak was 41.83 mV·s. When detecting the source gas without using the gas concentration module (100 ppb w/o PC), the integrated area of a reaction peak was 0.49 mV·s. Accordingly, a preconcentration factor was 85.4 when the gas concentration module was used.

In addition, the integrated area of the reaction peak which is 41.83 mV·s when detecting the gas after concentrating the source gas containing 100 ppb ethane using the gas concentration module (100 ppb w/ PC) is even larger than the integrated area of the reaction peak which is 24.69 mV·s when detecting the source gas containing 5 ppm ethane without using the gas concentration module (5 ppm w/o PC). Here, the preconcentration factor may be defined as a ratio of a reaction peak area measured when the gas concentration module is used with respect to a reaction peak area measured without using the gas concentration module.

As a result of the concentration test for methane and ethane, it can be seen that a target gas is well detected even when a source gas contains the target gas infinitesimally, for example at ppb level. This means that the concentration performance is significantly improved when the gas concentration module including the carbon foam is used.

<Performance Evaluation 3 of Gas Concentration Module>

The carbon nanotube foam obtained by Fabrication Example 1 was disposed in the chamber of the gas concentration module described with reference to FIGS. 3A and 3B, and a concentration performance test (GC-FID analysis) for ethane was executed while supplying droplets during the gas concentration process to control the relative humidity in the chamber to be 20%, 50%, and 80% by connecting the droplet generation module 300 to the gas concentration module.

FIGS. 11 and 12 are graphs illustrating results of gas concentration in the gas concentration module according to Performance Evaluation 3.

Referring to FIGS. 11 and 12, when detecting a gas while flowing a dried source gas including 5 ppm of ethane into a GC-FID system at a flow rate of 150 sccm without passing through the gas concentration module (5 ppm w/o PC, (A) in FIG. 11), the integrated area of a reaction peak was 50.4 mV·s. Meanwhile, when flowing a dried source gas containing 100 ppb of ethane into the gas concentration module, to which droplets were supplied to control the relative humidity to be 20%, 50%, and 80%, at a flow rate of 150 sccm for about 20 minutes, then increasing a temperature of the chamber of the gas concentration module to about 300° C. for 2 minutes using a heater pattern, and flowing the gas discharged therefrom into the GC-FID system to detect the gas (respectively, 100 ppb+RH 20% w/PC, 100 ppb+RH 50% w/PC, and 100 ppb+RH 80% w/PC, (C)), integrated areas of reaction peaks were 89.7 mV·s, 98.5 mV·s, and 103.2 mV·s, respectively.

In contrast, when flowing a dried source gas containing 100 ppb of ethane into the gas concentration module, to which droplets were not supplied, that is, the relative humidity of which was about zero, at a flow rate of 150 sccm for about 30 minutes, then increasing a temperature of the chamber of the gas concentration module to about 300° C. for 2 minutes using a heater pattern, and flowing the gas discharged therefrom into the GC-FID system to detect the gas (100 ppb w/PC for 30 min., (B)), an integrated area of reaction peak was 85.4 mV·s. From this, it can be seen that, compared to when the relative humidity was zero and concentration time was about 30 minutes (B), when the moisture was supplied and the concentration time was about 20 minutes (C), which is 10 minutes shorter than 30 minutes, the source gas was efficiently concentrated and the amount of detected gas rather increased. From this, it can be seen that the source gas was efficiently concentrated and the amount of detected gas increased when moisture was provided by supplying droplets, and more amount of gas was detected as the relative humidity increased.

In addition, it can be seen that when the relative humidity in the chamber increases, the gas concentration process may be efficiently performed in a relatively short time even though the content of the target gas in the source gas is low.

According to the embodiments of the present invention, the pressure drop in the gas concentration process may be reduced by using carbon foam having a large surface area, and the gas concentration efficiency may be improved by increasing the relative humidity in the chamber accommodating the carbon foam. In addition, the efficiency of desorption after the gas adsorption process may be improved by using the carbon foam having excellent thermal conductivity and the heating device.

As a result, even an extremely small amount of volatile organic compound gas contained at a ppb level in an exhaled breath gas or the atmosphere may be satisfactorily detected.

It will be apparent to those skilled in the art that various modifications can be made to the above-described embodiments of the present invention without departing from the spirit or scope of the invention. Thus, it is intended that the present invention covers all such modifications provided they come within the scope of the appended claims and their equivalents.

What is claimed is:

1. A gas concentration apparatus, comprising:
   a gas concentration module comprising:
   a base component including a chamber that accommodates carbon foam having linear carbon materials,
   a gas inlet connected to the chamber, and
   a gas outlet connected to the chamber;
   a heating device disposed on at least one side of the base component;
   a source gas injection line connected to the gas inlet of the gas concentration module; and
   a droplet generation module connected to the source gas injection line.

2. The gas concentration apparatus of claim 1, wherein the linear carbon materials are irregularly arranged, and the carbon foam further comprises a calcinated carbon layer coating outer surfaces of the linear carbon materials and a plurality of pores disposed between the linear carbon materials coated with the calcinated carbon layer.

3. The gas concentration apparatus of claim 1, wherein the heating device comprises a heater pattern.

4. The gas concentration apparatus of claim 1, wherein the heating device comprises a peltier device.

5. The gas concentration apparatus of claim 1, wherein the base component is a plate-type substrate, the chamber is formed in a trench shape in an upper surface of the substrate, and the gas inlet and the gas outlet are formed in a top plate covering the substrate.

6. The gas concentration apparatus of claim 1, wherein the source gas injection line is configured to supply a source gas to the gas inlet, wherein the source gas comprises a volatile organic compound.

7. The gas concentration apparatus of claim 1, wherein the droplet generation module comprises:
   a liquid storage unit configured to store a liquid;
   a droplet generator configured to generate droplets from the liquid storage unit; and
   a droplet discharge line connected to the source gas injection line.

8. The gas concentration apparatus of claim 7, wherein the liquid comprises water.

9. The gas concentration apparatus of claim 7, wherein the droplet generator is a bubble-generating gas injection line or an ultrasonic vibrator immersed in the liquid.

10. A method of operating a gas concentration apparatus, comprising:
    providing a gas concentration module including a base component having a chamber accommodating carbon foam containing linear carbon materials, a gas inlet connected to the chamber, a gas outlet connected to the chamber, and a heat-transfer device disposed on at least one side of the base component;
    supplying a source gas including a target gas through the gas inlet to concentrate the target gas in the carbon foam;
    increasing a relative humidity in the chamber at least one of before and while supplying the source gas; and
    heating the chamber with the heat-transfer device, which causes discharging the target gas concentrated in the carbon foam.

11. The method of claim 10, wherein the linear carbon materials are irregularly arranged, and the carbon foam comprises a calcinated carbon layer coating outer surfaces of the linear carbon materials and a plurality of pores disposed between the linear carbon materials coated with the calcinated carbon layer.

12. The method of claim 10, wherein the target gas comprises a volatile organic compound.

13. The method of claim 10, wherein the source gas comprises an exhaled breath gas.

14. The method of claim 10, wherein the heat-transfer device comprises a heater pattern or a peltier device.

15. The method of claim 10, wherein the heat-transfer device comprises a peltier device, wherein the method further comprises:
   cooling the chamber with the peltier device while supplying the source gas, and
   heating the chamber with the peltier device while discharging the target gas concentrated in the carbon foam.

16. The method of claim 10, wherein increasing the relative humidity in the chamber includes supplying droplets to the chamber.

17. The method of claim 10, wherein increasing the relative humidity in the chamber includes lowering temperature inside the chamber.

* * * * *